(12) United States Patent
Creazzo

(10) Patent No.: US 9,233,377 B2
(45) Date of Patent: Jan. 12, 2016

(54) METHOD, SYSTEM, AND APPARATUS FOR ALIGNING THE ANGLE OF A POLAR COORDINATE SYSTEM DEVICE TO THE AXIS OF AN END-EFFECTOR

(75) Inventor: Thomas Creazzo, Tuxedo, NY (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 191 days.

(21) Appl. No.: 14/111,061

(22) PCT Filed: Mar. 2, 2012

(86) PCT No.: PCT/US2012/027473
§ 371 (c)(1),
(2), (4) Date: Oct. 10, 2013

(87) PCT Pub. No.: WO2012/141816
PCT Pub. Date: Oct. 18, 2012

(65) Prior Publication Data
US 2014/0045673 A1  Feb. 13, 2014

Related U.S. Application Data

(60) Provisional application No. 61/474,788, filed on Apr. 13, 2011.

(51) Int. Cl.
*B04B 9/14* (2006.01)
*B25J 9/02* (2006.01)
(Continued)

(52) U.S. Cl.
CPC . *B04B 9/14* (2013.01); *B25J 9/023* (2013.01); *B25J 9/1692* (2013.01);
(Continued)

(58) Field of Classification Search
CPC ...... B04B 9/14; B04B 2011/046; B25J 9/023; B25J 9/1692; G05B 2219/40082; G01N 2035/00495; G01N 35/0099
USPC .................... 494/16, 20, 37, 82, 85
See application file for complete search history.

(56) References Cited

U.S. PATENT DOCUMENTS 4,611,843 A * 9/1986 Burger et al. ............... 294/86.4
4,799,853 A   1/1989 Wrobbel et al.
(Continued)

FOREIGN PATENT DOCUMENTS

KR   20040001439 A * 1/2004 ............ B04B 5/0414

OTHER PUBLICATIONS

PCT International Search Report and Written Opinion dated Aug. 16, 2012 (15 Pages).
(Continued)

*Primary Examiner* — Charles Cooley
*Assistant Examiner* — Shuyi S Liu
(74) *Attorney, Agent, or Firm* — Preti, Flaherty, Beliveau & Pachios LLP

(57) ABSTRACT

A method, system, and apparatus for aligning the index angle of a polar coordinate system device, such as the rotor of a centrifuge, with the vertical axis of a Cartesian coordinate system device, such as a robotic end-effector. The apparatus includes a first registration device, that is removably attached to the gripping means of the end-effector and a second registration device, that is removably insertable into a pivoting platform, such as a bucket to a centrifuge rotor. As the first registration device is lowered into the second registration device, the fixed orientation of the notches of the second registration device and the rigid nature of the first registration device cause a linear ball slide to displace and the bucket to rotate until the primary axis of the linear ball slide is in compliance with the cross pin axis of the first registration device.

17 Claims, 5 Drawing Sheets

(51) Int. Cl.
*B25J 9/16* (2006.01)
*B04B 11/04* (2006.01)
*G01N 35/00* (2006.01)

(52) U.S. Cl.
CPC ...... *B04B 2011/046* (2013.01); *G01N 35/0099* (2013.01); *G01N 2035/00495* (2013.01); *G05B 2219/40082* (2013.01)

(56) References Cited

U.S. PATENT DOCUMENTS

| | | |
|---|---|---|
| 5,163,802 A | 11/1992 | Poinelli |
| 5,366,340 A * | 11/1994 | Vo et al. ............... 414/732 |
| 5,452,521 A | 9/1995 | Neiwmierzycki |
| 5,588,794 A | 12/1996 | Panyard |
| 6,591,160 B2 | 7/2003 | Hine et al. |
| 7,681,466 B2 * | 3/2010 | Miller et al. ............ 73/864.31 |
| 2004/0002415 A1* | 1/2004 | Jang ....................... 494/10 |
| 2007/0065144 A1 | 3/2007 | Hofmeister et al. |
| 2008/0228319 A1 | 9/2008 | Ding et al. |
| 2013/0190161 A1* | 7/2013 | Gaudio et al. ............ 494/16 |

OTHER PUBLICATIONS

Extended European Search Report dated Jan. 5, 2015 of corresponding European Patent Application No. 12771726.2, 6 Pages.

\* cited by examiner

METHOD, SYSTEM, AND APPARATUS FOR ALIGNING THE ANGLE OF A POLAR COORDINATE SYSTEM DEVICE TO THE AXIS OF AN END-EFFECTOR

CROSS-REFERENCE TO RELATED-APPLICATIONS

Not Applicable

STATEMENT REGARDING FEDERALLY SPONSORED RESEARCH OR DEVELOPMENT

Not Applicable

BACKGROUND OF THE INVENTION

The invention provides a method, system, and apparatus for aligning the index angle of a polar coordinate system device and more specifically, to a method, system, and device for aligning the index angle of a pivoting platform within a rotating device, such as the rotor of a centrifuge, with a vertical axis of a robotic end-effector.

Centrifuges are well-known devices that are used to rotate samples contained in test tubes or cassettes holding a plurality of test tubes at relatively high speeds. Centrifuges that are structured and arranged for cassettes typically include a centrifuge rotor having a plurality of arms with trunions from which can be suspended a pivoting platform, e.g., a bucket, for holding one or more cassettes. As the rotor rotates, the pivoting platforms suspended from the trunions pivot about an axis so that the test tubes in the cassettes also pivot to horizontal or near horizontal orientations.

Because centrifuges are designed to operate at high rates of speed, e.g., 4500 revolutions per minute (RPM), to ensure that the centrifuge rotor is in balance, it is important that the cassettes are inserted into the buckets and the buckets are positioned on the trunions precisely.

As robotic arms are increasingly being used for loading and unloading centrifuges, positioning cassettes and buckets requires that the end-effectors of the robotic arms, i.e., robotic grippers and the like, have a reference system that complies with that of the pivoting platform of the centrifuge rotor. This is complicated by the fact that, conventionally, end-effectors lack adequate compliance in all degrees of freedom, except for the vertical axis. Accordingly, it would be desirable to have a method, system, and apparatus for aligning the index angle of a polar coordinate system device, e.g., the pivoting platform of the centrifuge rotor, with the vertical axis of the robotic gripper.

SUMMARY OF THE INVENTION

A method, system, and apparatus for aligning the index angle of a polar coordinate system device, e.g., the rotor of a centrifuge, with the vertical axis of a robotic end-effector are disclosed. The apparatus includes a first registration device, e.g., a T-bar registration portion, that is removably attachable to the gripping system of the robotic end-effector and a second registration device, e.g., a V-block registration device, that is removably insertable into a pivoting platform, e.g., a bucket to a centrifuge rotor.

The first, i.e., T-bar, registration device includes an upper, coaxial pair and a lower, coaxial pair of registration (cross) pins that are precisely machined so that the axis of the upper pair is orthogonal to the axis of the lower pair of cross pins. The upper pair of cross pins is structured and arranged to be engaged by the gripping system of the robotic end-effector. Accordingly, when properly installed in the gripping system of the robotic end-effector, the first, T-bar registration device is oriented along the vertical axis of the robotic arm. Moreover, the axis of the lower pair of cross pins, i.e., the "cross pin axis", is orthogonal to the vertical axis.

The second, i.e., V-block, registration device includes a substantially U-shaped V-block and a base portion. The V-block registration device is mechanically attached to a linear ball slide. The base portion includes an alignment step-down along which the linear ball slide can move. The V-block includes a pair of notches into each of which one of the pair of lower cross pins is insertable.

When the first, T-bar registration device is lowered into the second, V-block registration device, the fixed orientation of the notches of the second, V-block registration device and the rigid nature of the first, T-bar registration device cause the V-block registration device to be displaced along a secondary axis on the linear ball slide, while the lower pair of cross-pins slides in the V-block as the bucket rotates. Simultaneously, as a result of the mechanical interaction of the T-bar registration device and the V-block registration device, the rotor of the centrifuge rotates. When the T-bar registration device is properly seated in the V-block registration device, the index angle of the centrifuge rotor is aligned with the vertical axis of the robotic end-effector and a centrifuge indexing device stores the index angle in memory.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
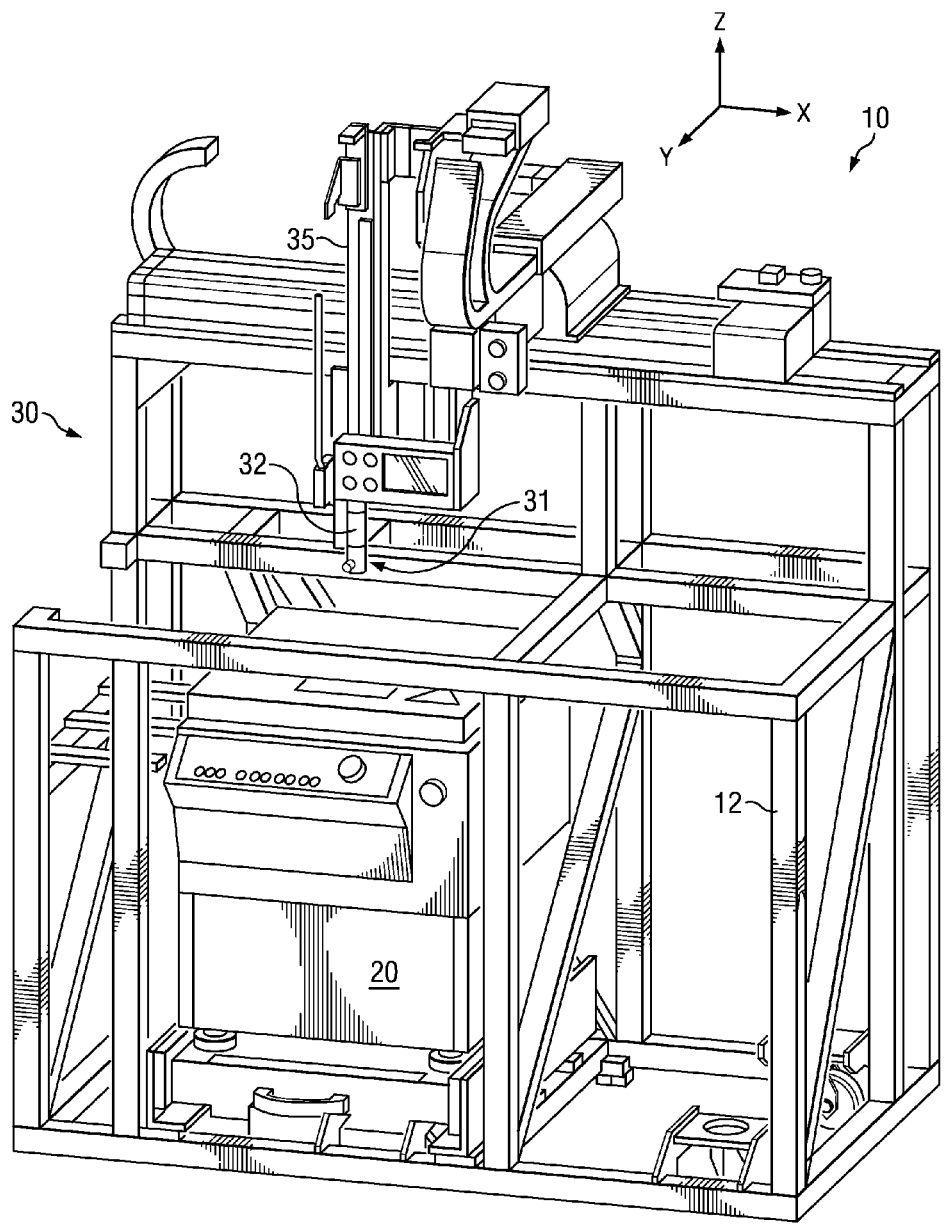
FIG. 1 shows a diagrammatic view of a centrifuge assembly and robotic arm with an end-effector.

Referring to FIG. 1, there is shown a centrifuge assembly 10 that includes a centrifuge system 20, a frame assembly 12, and a multi-axis, e.g., three axis, robotic arm 30. The robotic arm 30 is structured and arranged to move in three, mutually orthogonal directions. A gantry portion 35 having an end-effector 32 at a distal end 31 thereof defines a vertical alignment axis. The end-effector 32 can be a gripper-type end-effector 32 that can be adapted to insert and remove individual containers, e.g., test tubes, respectively, into or from a cassette and/or to insert and remove individual cassettes, respectively, into or from a pivoting platform, e.g., a centrifuge bucket, that is rotatably attached to a polar coordinate system device, such as a centrifuge rotor. Although, the invention will be described in terms of a centrifuge rotor, those skilled in the art can appreciate the universal application of the teachings of this disclosure to any polar coordinate system device.

When interfacing a two-dimensional (r, θ), polar coordinate system device, such as a rotor bucket of a centrifuge rotor, with a three-dimensional, Cartesian coordinate system device, one must simultaneously orient a polar coordinate system alignment device with respect to the x- and y-coordinates of the Cartesian coordinate system device while, at the same time, aligning it with respect to the vertical (z-) alignment axis, such as a robotic end-effector 32. An alignment apparatus, alignment method, and a system so aligned are described hereinbelow.

Figure 2:
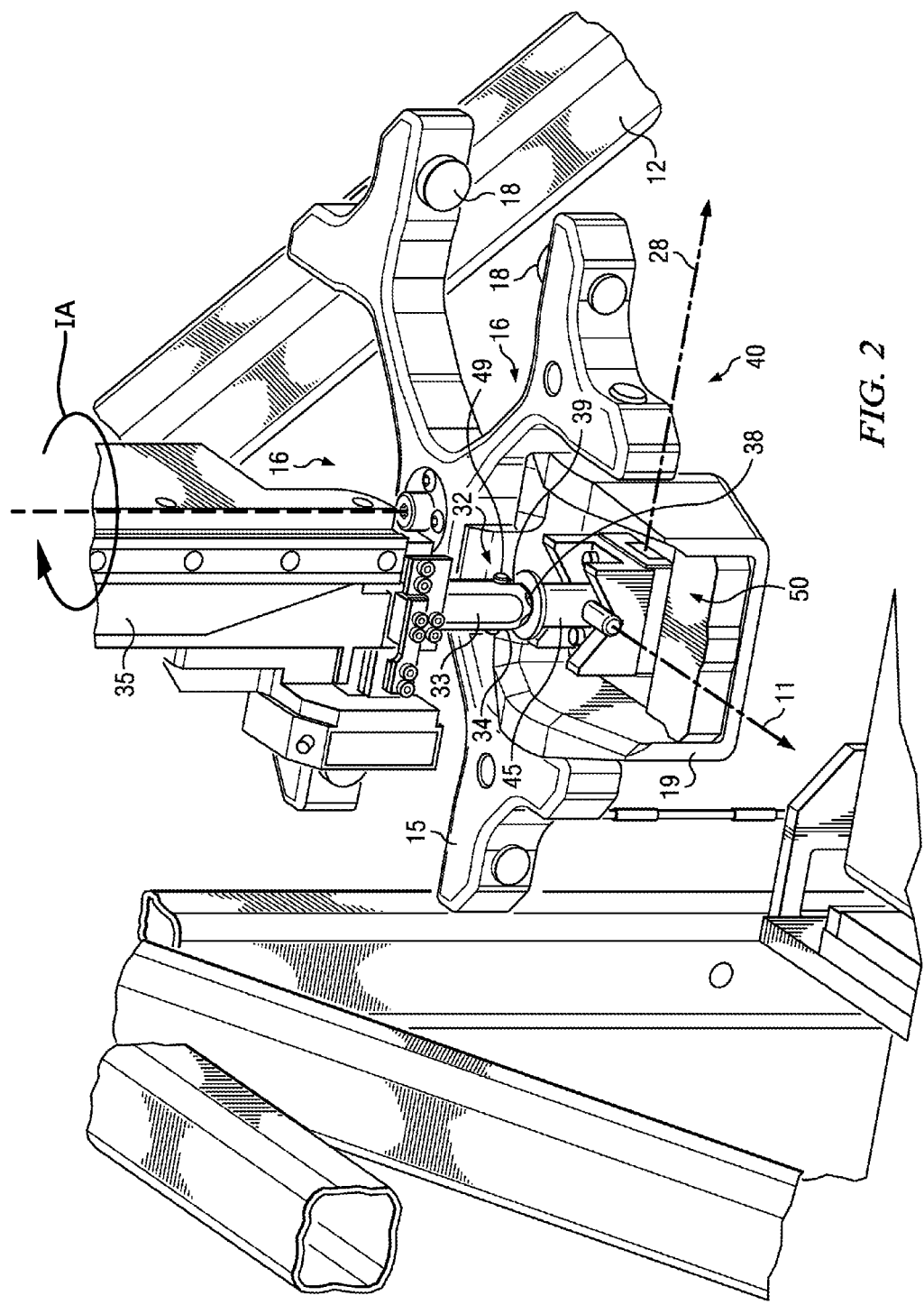
FIG. 2 shows a diagrammatic view of a polar coordinate system device and an aligning system for the end-effector of FIG. 1.

Referring to FIG. 2, there is shown an apparatus for aligning an index angle IA of a polar coordinate system device with a vertical axis of a Cartesian coordinate system device. More specifically, FIG. 2 shows a two-dimensional, polar coordinate system device, e.g., a rotor bucket 19 of a centrifuge rotor 15, and a three-dimensional, Cartesian coordinate system device, e.g., a robotic end-effector 32. The centrifuge rotor 15 is structured and arranged to include a plurality, e.g., four, stations 16. A pair of cylindrical trunions 18 is provided within each station 16. Trunion pairs 18 are structured and arranged to rotatably support a centrifuge bucket 19. Each centrifuge bucket 19 is structured and arranged to accommodate a cassette (not shown) containing at least one test tube (not shown) and, moreover, to pivot about the pair of trunions 18 during high-speed rotation of the centrifuge rotor 15.

The robotic end-effector 32 is removably attached at the distal end 31 (FIG. 1) of the robotic arm gantry 35 that defines the vertical (z-axis) alignment. The end-effector 32 includes a first pair of opposing fingers 34 that are structured and arranged to pick up individual test tubes and a second pair of opposing fingers 33 for picking up cassettes. Each opposing finger 34 defines a slotted opening 39. Optionally, the first pair of opposing fingers 34 can include a plurality of beveled tips 38 to facilitate picking up individual test tubes.

Figure 3:
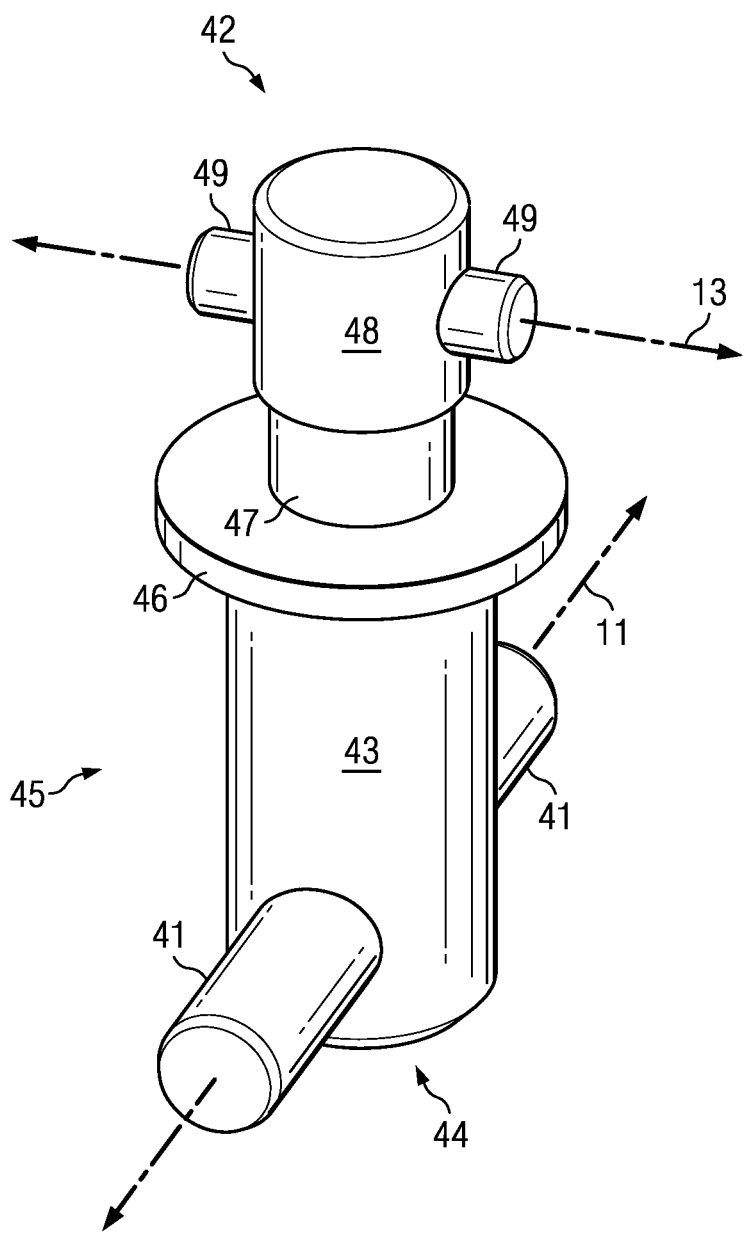
FIG. 3 shows a diagrammatic view of a T-bar registration device in accordance with the present invention.

An alignment system 40 for "truing up" the rotor 15 includes a V-block registration device 50 (detail shown in FIG. 4) and a T-bar registration device 45 (detail shown in FIG. 3). The V-block registration device 50 is removably insertable into a bucket 19. The T-bar registration device 45 is removably attachable to the first pair of opposing fingers 34 via the pair of slotted openings 39.

Referring to FIG. 3, the T-bar registration device 45 will be described. Preferably, the T-bar registration device 45 is machined from stainless steel or other suitable, strong, rigid metal. The T-bar registration portion 45 includes a first pair of engagement (cross) pins 41 that are disposed at a distal end 44 and a second pair of engagement (cross) pins 49 that are disposed at a proximal end 42. The first pair of cross pins 41 is fixedly attached to a first vertical bar portion 43 and is adapted to interface with the V-block registration device 50. The first pair of cross pins 41 defines a cross pin axis 11.

The second pair of engagement cross pins 49 is fixedly attached to a second vertical bar portion 48 and is adapted to interface with the slotted openings 39 of the opposing fingers 34 of the gripping system. The second vertical bar portion 48 is further machined to include a recessed gripping portion 47 that makes it easier for the first pair of opposing fingers 34 to grab and securely hold the T-bar registration device 45. A disk-like flange 46 is provided between the first 43 and second 48 vertical bar portions, to prevent the T-bar registration device 45 from rocking or rotating while it is gripped by the first pair of opposing fingers 34. The first 41 and second 49 pairs of cross pins (registration and engagement, respectively) are precision machined to be at a 90 degree angle from each other, which is to say that the cross pin axis 11 is orthogonal to an engagement pin axis 13 of the second pair of engagement cross pins 49.

Figure 4:
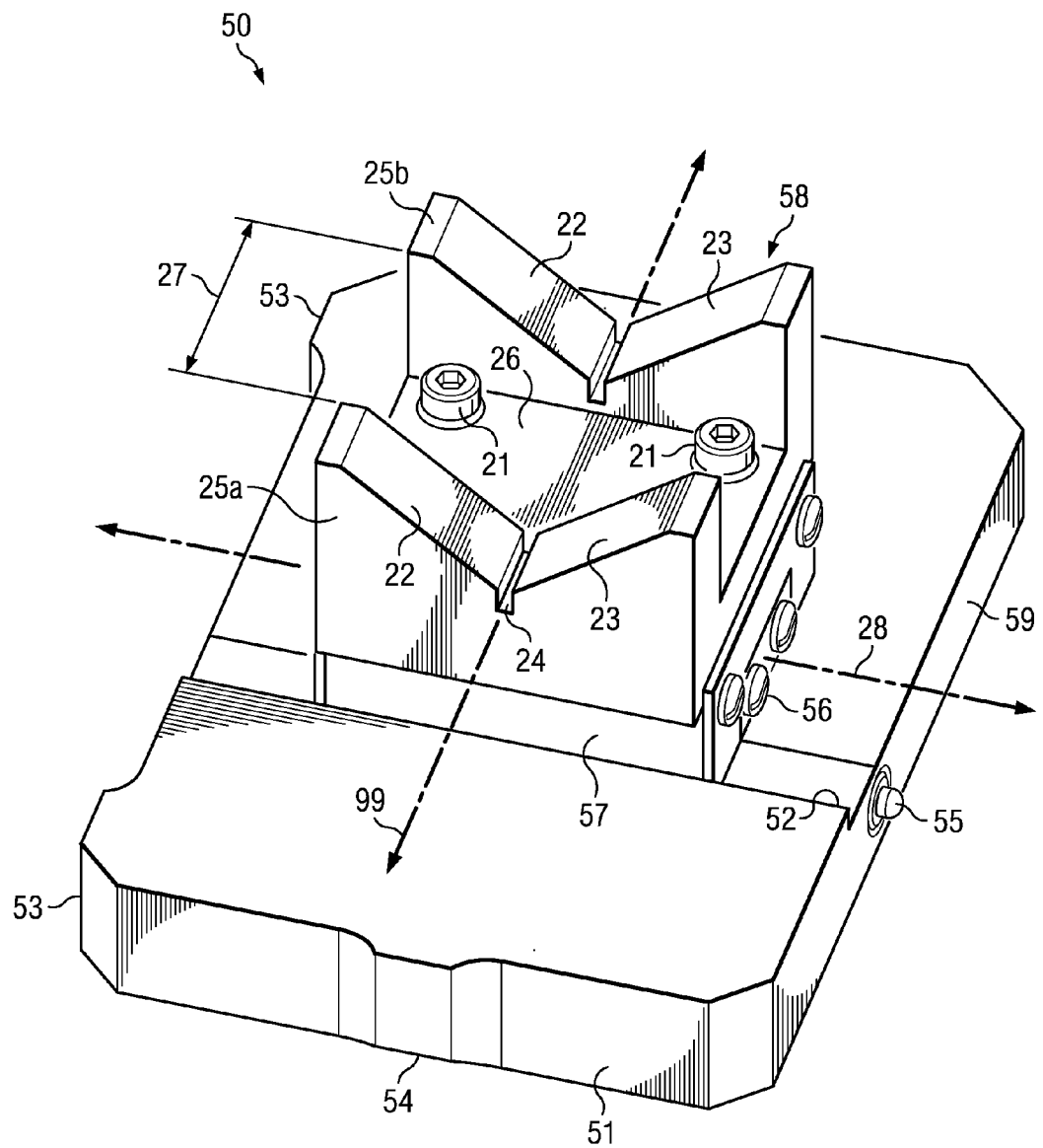
FIG. 4 shows a diagrammatic view of a V-block registration device in accordance with the present invention.

Referring to FIG. 4, the V-block registration device 50 will be described. The V-block registration device 50 includes a platform (base) portion 51, a linear ball slide 56, and a V-block portion 58.

The base portion 51 is a stepped substrate having an alignment step-down (or "banking surface") 52 along which the linear ball slide 56 traverses. Spring-loaded ball plungers 55 are provided in the side walls 59 of the base portion 51 and are structured and arranged to bias projections 53 and 54 against the walls of the bucket 19 after the V-block registration device 50 has been inserted into a bucket 19. Only one spring-loaded ball plunger 55 is shown in FIG. 4. The other spring-loaded ball plunger (not shown) is disposed along the top side of the base 51 and hidden behind the V-block portion 58. FIG. 4 shows two projections 53 at the corners of one side of the base 51 and a single projection 54 at the center of another side of the base 51. The number and location of projections on the sides of the base 51, however, are shown for illustrative purposes only.

Preferably, the V-block portion 58 is manufactured from a robust plastic or thermo-plastic, e.g., polyoxymethylene (POM), aluminum, and so forth. The V-block portion 58 is U-shaped, having a first perpendicular or substantially perpendicular V-block leg 25a and a second perpendicular or substantially perpendicular V-block leg 25b, which are fixedly attached to a planar bottom portion 26. The width 27 of the planar bottom portion 26, i.e., the distance between the V-block legs 25a and 25b, is slightly greater than the diameter of the first vertical bar portion 43 of the T-bar registration device 45 to provide some free-play. The planar bottom portion 26 is mechanically attached to the linear ball slide 56, e.g., using a plurality of fasteners 21, such as screws, nuts, rivets, and the like.

Each of the V-block legs 25a and 25b includes a V-shaped notch area that is structured and arranged to accommodate the first pair of cross pins 41 of the T-bar registration device 45. Each notch area includes a first 22 and a second 23 planar surface that intersect at the bottom of the notch area. Preferably, the angle defined by the planar surfaces 22, 23 at the notch is between about 100 and 140 degrees, and more preferably, about 120 degrees. Optionally, a cross-cut channel 24 can be provided at the intersection at the bottom of the notch area. The cross-cut channel 24 is structured and arranged to better accommodate first cross pins 41 of various diameter. Longitudinally, the cross-cut channels 24 are oriented coaxially along a primary axis 99.

The linear ball slide 56 can be an off-the-shelf linear ball slide such as those manufactured by Del-Tron Precision, Inc. of Bethel, Conn. A longitudinal side 57 of the linear ball slide 56 moves along the secondary or circumferential axis 28 and is coupled to and in contact with the stepped portion 52 of the base 51.

Having described some of the components making up an alignment apparatus and system, a method of aligning the index angle IA of a polar coordinate system device to coincide with the vertical axis of an end-effector, to true-up the polar coordinate system device with respect to the Cartesian coordinate system device, will be described. As previously mentioned, the method of "truing-up" the polar coordinate system device, e.g., the centrifuge rotor, sets the centrifuge rotor at the proper angle so that the longitudinal or primary axis of the bucket is true to the vertical axis of the robotic end-effector. This ensures that the rotational angle of the rotor is correctly set before the x- and y-coordinates of the robotic arm are properly aligned with the bucket and rotor.

Figure 5:
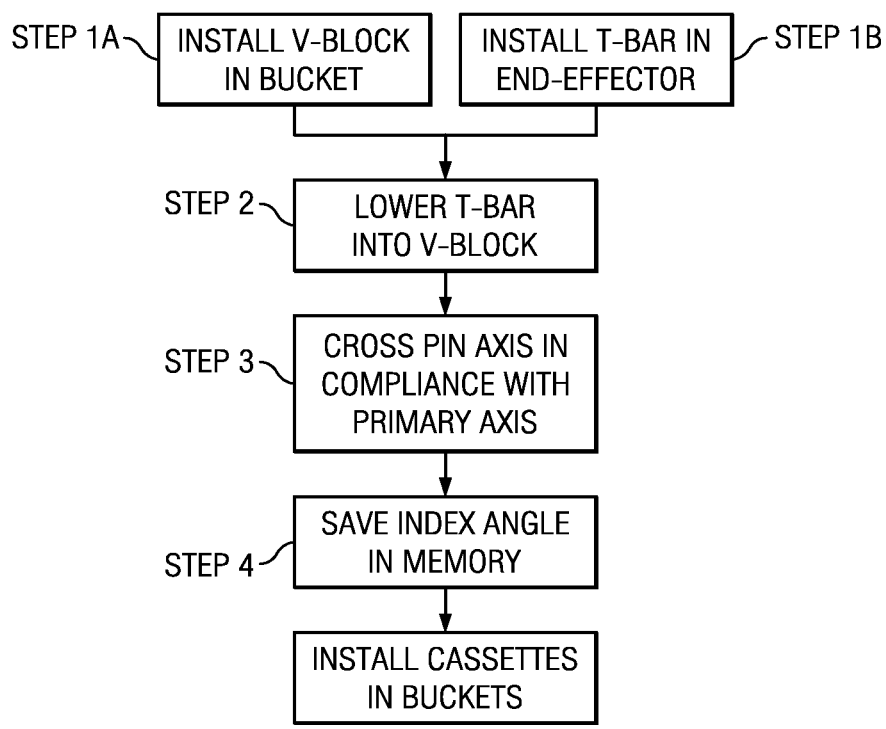
FIG. 5 shows a flow chart of a method for aligning the index angle of a polar coordinates system device with the vertical axis of a Cartesian coordinate device in accordance with the present invention.

Referring to FIG. 5, in a first step a V-block registration device is installed in a rotor bucket (STEP 1A), e.g., manually, and a T-bar registration device is installed, e.g., manually, in the gripping system of an end-effector (STEP 1B). The robotic arm then lowers the end-effector and T-bar registration device in a vertical direction into the centrifuge towards the V-block registration device (STEP 2). Finally, the T-bar registration device is forced into the V-block registration device until the cross pin axis is in compliance with the primary axis of the platform (STEP 3). This is referred to as "docking".

The process of docking the T-bar registration device with the V-block registration device can result in one or more of the following actions: the V-block registration device can slide or displace bi-directionally along the banking surface of the base portion; the T-bar registration device can slide or displace radially within the V-block registration device; and/or the base portion of the V-block registration device and the bucket can rotate to an angle that is defined by the engagement of the first pair of cross pins and the V notches.

Once the primary axis and cross pin axis are in compliance, the platform, and, hence, the bucket and rotor, and the end-effector are aligned, which is to say "true." The location of the bucket and rotor, i.e., a programmed index angle, can then be saved in memory (STEP 4), e.g., the control memory of the centrifuge. Henceforth, the robotic end-effector can operate in all three dimensions within the centrifuge to grasp cassettes having a plurality of test tubes and/or to grasp discrete test tubes disposed in a cassette with a high degree of accuracy.

Although preferred embodiments of the invention have been described above, it will be recognized and understood that various modifications may be made in the invention and that the appended claims are intended to cover all such modifications that fall within the spirit and scope of the invention.

What is claimed is:

1. An apparatus for aligning an index angle of a polar coordinate system device with a vertical axis of a Cartesian coordinate system device, the apparatus comprising:
   a first registration device that is attached to the Cartesian coordinate system device such that the first registration device is oriented along the vertical axis of the Cartesian coordinate system device, the first registration device including a pair of coaxial registration pins whose axis defines a cross pin axis; and
   a second registration device that is removably inserted into a pivoting platform within the polar coordinate system device, the second registration device including a docking area that is structured and arranged to accommodate the pair of coaxial registration pins of the first registration device,
   wherein the docking area includes a U-shaped or substantially U-shaped portion that includes a base portion and two vertical or substantially vertical legs, each of the legs having a V-notched portion that is structured and arranged to interface with the pair of coaxial registration pins.

2. The apparatus as recited in claim 1, wherein the second registration device includes a movable device that is adapted to move along a circumferential axis with respect to the polar coordinate system device, and a stepped platform that provides an alignment step-down that defines the circumferential axis.

3. The apparatus as recited in claim 2, wherein the movable device is a linear ball slide.

4. The apparatus as recited in claim 2, wherein the index angle is adapted to be aligned when the circumferential axis is perpendicular to the cross pin axis.

5. The apparatus as recited in claim 1, wherein the V-notched portion of at least one of the vertical legs has a bottom portion and a cross-cut channel through the vertical leg is provided at the bottom portion.

6. The apparatus as recited in claim 1, wherein the first registration device is a T-bar registration device having a proximal end and a distal end, and
   wherein the pair of coaxial registration pins is disposed at the distal end of the T-bar registration device and adapted to interface with the docking area and a pair of engagement pins is disposed at the proximal end of the T-bar registration device and adapted to interface with the Cartesian coordinate system device.

7. The apparatus as recited in claim 6, wherein the pair of coaxial registration pins is orthogonal to the pair of engagement pins.

8. The apparatus as recited in claim 1, wherein the Cartesian coordinate system device is a robotic end-effector.

9. A method of at least one of aligning and truing an index angle of a rotating polar coordinate system device with a vertical axis of a Cartesian coordinate system device, the method comprising:
   installing a first registration device having a first axis in the Cartesian coordinate system device so that the first axis of the first registration device is aligned with the vertical axis of the Cartesian coordinate system device;
   installing a second registration device within a pivoting platform disposed on a rotor portion of the rotating polar coordinate system device;
   lowering the first registration device along the first axis; and
   interfacing a pair of coaxial registration pins that defines a cross pin axis in the first registration device with the second registration device until a circumferential axis of the pivoting platform is orthogonal to, or in compliance with, the cross pin axis of the pair of coaxial registration pins of the first registration device,
   wherein the second registration device includes a stepped platform that provides an alignment step-down that defines the circumferential axis.

10. The method as recited in claim 9, wherein interfacing includes one or more of:
    moving or displacing the second registration device relative to a radial axis of the pivoting platform, the radial axis being orthogonal to the circumferential axis;
    moving or displacing the first registration device relative to the circumferential axis; and
    rotating the second registration device and the pivoting platform.

11. An improvement to a centrifuge assembly that includes a three-dimensional, Cartesian coordinate gantry and a centrifuge system with a two-dimensional, polar coordinate rotor, the rotor having a plurality of pivoting platforms and the gantry having a robotic end-effector, having a vertical alignment axis, and having a gripping system, the improvement comprising:
    a first registration device that is releasably attached to the gripping system of the end-effector such that the first registration device is oriented along the vertical axis of the robotic end-effector, the first registration device including a pair of coaxial registration pins whose axis defines a cross pin axis; and
    a second registration device that is removably inserted into one of the pivoting platforms, the second registration device including a docking area that is structured and arranged to accommodate the pair of coaxial registration pins of the first registration device,
    wherein the docking area includes a U-shaped or substantially U-shaped portion that includes a base portion and two vertical or substantially vertical legs, each of the legs having a V-notched portion that is structured and arranged to interface with the pair of coaxial registration pins.

12. The improvement as recited in claim 11, wherein the second registration device further is mechanically attached to a movable device that is adapted to move along a circumferential axis with respect to the polar coordinate system device, and the second registration device includes a stepped platform that provides an alignment step-down that defines the circumferential axis.

13. The improvement as recited in claim 12, wherein the movable device is a linear ball slide.

14. The improvement as recited in claim 12, wherein the index angle is adapted to be aligned when the circumferential axis is perpendicular to the cross pin axis.

15. The improvement as recited in claim 11, wherein the V-notched portion of at least one of the vertical legs has a bottom portion and a cross-cut channel through the vertical leg is provided at the bottom portion.

16. The improvement as recited in claim 11, wherein the first registration device is a T-bar registration device having a proximal end and a distal end, and wherein the pair of coaxial registration pins is disposed at the distal end of the T-bar registration device and adapted to interface with the docking area and a pair of engagement pins is disposed at the proximal end of the T-bar registration device and adapted to interface with the Cartesian coordinate system device.

17. The improvement as recited in claim 16, wherein the pair of coaxial registration pins is adapted to be orthogonal to the pair of engagement pins.

\* \* \* \* \*